United States Patent [19]
Sanders

[11] 3,948,273
[45] Apr. 6, 1976

[54] ENDOTRACHEAL TUBE HAVING A NON-STICKING INNER SURFACE

[75] Inventor: David H. Sanders, Deerfield, Ill.

[73] Assignee: Medical Engineering Corporation, Racine, Wis.

[22] Filed: Sept. 13, 1974

[21] Appl. No.: 505,570

[52] U.S. Cl. ............................................. 128/351
[51] Int. Cl.² ................ A61M 1/00; A61M 16/00; A61M 25/00
[58] Field of Search......... 128/261, 263, 349 R, 351

[56] References Cited
UNITED STATES PATENTS

| | | | |
|---|---|---|---|
| 813,918 | 2/1906 | Schmitz | 138/114 X |
| 3,015,332 | 1/1962 | Brecht | 128/263 |
| 3,169,527 | 2/1975 | Sheridan | 128/349 R |
| 3,756,244 | 9/1973 | Kinnear et al. | 128/351 |

Primary Examiner—Channing L. Pace
Attorney, Agent, or Firm—Ronald E. Barry

[57] ABSTRACT

An endotracheal or tracheostomy tube having a non-sticking inside surface for allowing for the free movement of a suction catheter through the tube. The non-sticking surface is in the form of a series of grooves separated by ridges having thin edges extending through the length of the tube for engaging the surface of the catheter.

2 Claims, 2 Drawing Figures

ENDOTRACHEAL TUBE HAVING A NON-STICKING INNER SURFACE

BACKGROUND OF THE INVENTION

A patient requiring intermittent anesthesia, air way patency or positive pressure ventilation may have an endotracheal tube inserted into the trachea by way of the mouth or nose or by way of a surgically created opening in the trachea. The distal end of the tube is sometimes encircled by an inflatable cuff to provide a seal against the wall of the trachea. After insertion of the tube, foreign matter such as mucous often accumulates near the distal end of the tube. In order to remove any accumulation of foreign matter, a suction catheter is inserted into the trachea through the endotracheal tube until the end of the catheter projects beyond the distal end of the tube. Suction catheters (especially silicone, polyvinyl chloride, or silicone treated) are small and thin-walled and easily stick to the inside surface of the endotracheal tube. Since any movement of the endotracheal tube is undesirable, it is essential that the catheter move freely. Various lubricants have been used to eliminate sticking. However, the lubricants are then left in the tube and can be forced into the trachea during the ventilating cycle.

SUMMARY OF THE INVENTION

The endotracheal tube of the present invention overcomes the above problem by providing a non-sticking surface on the inside of the tube. The non-sticking surface is in the form of a series of parallel grooves separated by thin ridges which extend through the full length of the tube. The suction catheter ridges on the edges of the ridges provided between the grooves thus reducing the surface area contact between the catheter and the tube to a minimum.

DRAWINGS

DESCRIPTION OF THE INVENTION

Figure 1:
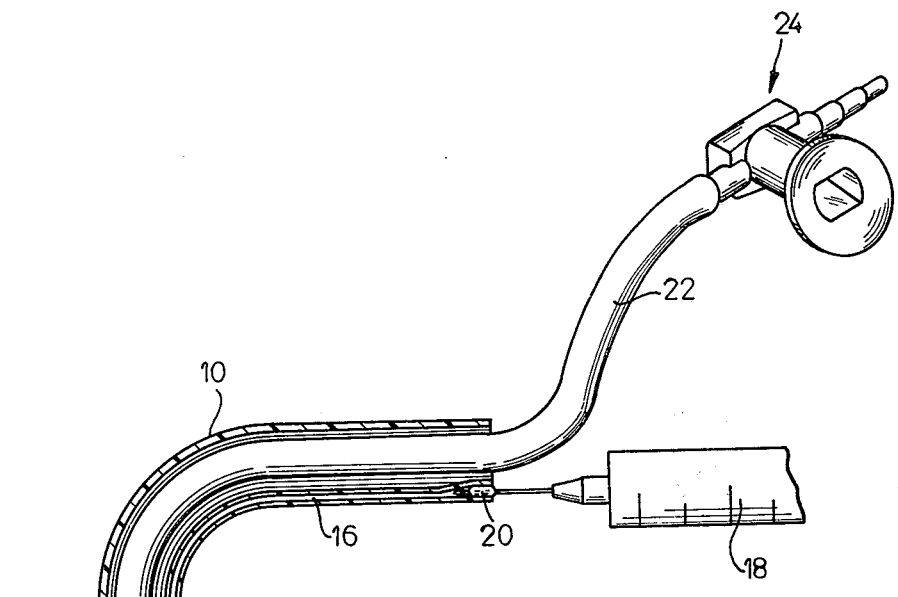
FIG. 1 is a side view in section showing an endotracheal tube with a suction catheter extending through the tube.
Figure 2:
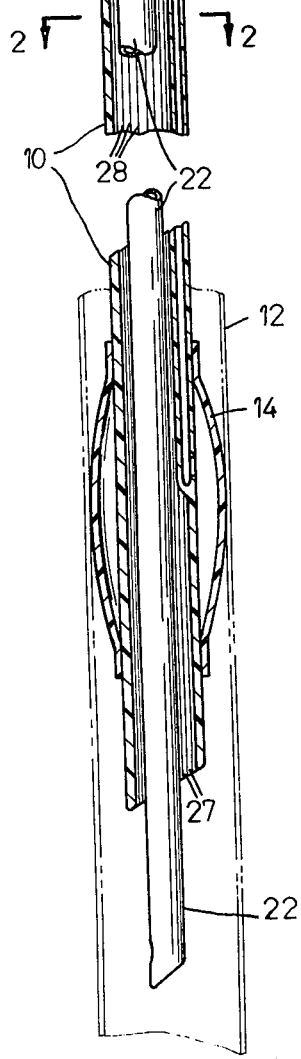
FIG. 2 is an enlarged cross-sectional view taken on line 2—2 of FIG. 1.
Figure 2:
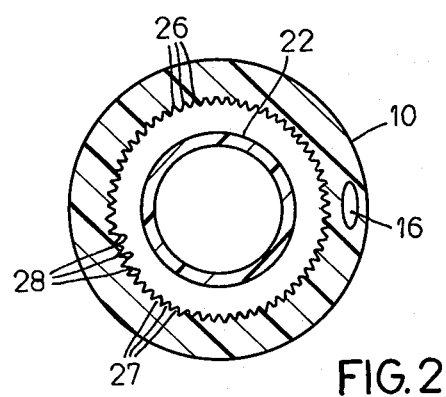

As seen in the drawings, a flexible endotracheal or tracheostomy tube 10 is shown inserted into a trachea 12 with the outer or proximal end exposed for connection to a breathing apparatus for forcing air periodically into the lung. The tube 10 is made from a rubber material and is provided with an elastic cuff 14 near its inner or distal end which is inflated to seal the endotracheal tube in the trachea. The cuff 14 can be inflated through a lumen 16 provided in the wall of the catheter by means of a syringe 18. A self-sealing plug or valve 20 of the type shown in copending application Ser. No. 477,307, filed June 7, 1974 and entitled "An Implantable Prosthesis Having a Self-Locating Valve" is provided at the proximal end of the lumen 16 for sealing the lumen after inflation. After inflation, the syringe is removed and is reinserted through the valve 20 when the cuff is deflated to remove the tube from the trachea.

In the event of an accumulation of foreign matter such as mucous in the trachea 12 adjacent the distal end of the tube 10, a suction catheter 22 is forced through the endotracheal tube into the trachea. The suction catheter 22 must be run through the entire length of the tube in order to project far enough into the trachea to remove the foreign material. The proximal end of the suction tube is connected to a vacuum control valve 24 for drawing the foreign material out of the trachea. The catheter is also formed from a rubber material.

In accordance with the invention, the endotracheal tube is provided with means on its inner surface for preventing sticking of the suction catheter to the endotracheal tube. Such means is in the form of a series of grooves 26 provided around the inside surface of the tube and extending throughout its full length. The grooves 26 are separated by means of ridges 27 having thin edges 28 at their inner ends for engaging the outer surface of the suction catheter. The surface area contact between the inner surface of the endotracheal tube and the suction catheter is thereby reduced to a minimum.

In a preferred embodiment the inner edges of the ridges 27 should be spaced apart approximately 0.010 of an inch and the grooves should have a depth of 0.010 of an inch. The suction catheter normally has an outside diameter substantially smaller than the inside diameter of the catheter in order to provide a space for the continued application or air pressure around the outside of the catheter.

In an alternative embodiment of the invention, the means for preventing sticking is provided on the outside surface of the suction catheter. In this embodiment, the non-sticking means is in the form of a number of ridges which terminate in thin edges which provide line contact between the catheter and the inside surface of the tube. By reducing the surface area contact between the tube and the catheter, the sticking problem is substantially eliminated.

I claim:

1. A tracheostomy or endotracheal tube formed from a flexible rubber material and including a series of thin ridges on the inner surface of said tube for preventing sticking between said tube and a suction catheter having an outer diameter substantially smaller than the internal diameter of said series of ridges for preventing sticking on insertion of the catheter into said tube.

2. An endotracheal or tracheostomy tube and a suction catheter adapted to be inserted through the tube, a continuous series of closely spaced ridges integral with said catheter for reducing the surface area contact between the inside surface of the tube and the outside surface of the catheter, said series of ridges having an outside diameter substantially smaller than the inside diameter of said tube, each ridge terminating in a thin line extending the full length of said tube or catheter.

* * * * *